United States Patent
Hibino et al.

(10) Patent No.: US 8,803,516 B2
(45) Date of Patent: Aug. 12, 2014

(54) EDDY CURRENT TESTING METHOD AND APPARATUS FOR INSPECTING AN OBJECT FOR FLAWS

(75) Inventors: Takashi Hibino, Narita (JP); Takashi Fujimoto, Narita (JP); Keisuke Komatsu, Narita (JP); Yoshiyuki Nakao, Osaka (JP); Makoto Takata, Osaka (JP); Makoto Sakamoto, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 445 days.

(21) Appl. No.: 13/140,845

(22) PCT Filed: Dec. 14, 2009

(86) PCT No.: PCT/JP2009/070813
§ 371 (c)(1),
(2), (4) Date: Aug. 24, 2011

(87) PCT Pub. No.: WO2010/073926
PCT Pub. Date: Jul. 1, 2010

(65) Prior Publication Data
US 2012/0161758 A1 Jun. 28, 2012

(30) Foreign Application Priority Data
Dec. 24, 2008 (JP) .................................. 2008-328867

(51) Int. Cl.
*G01R 33/12* (2006.01)
*G01N 27/90* (2006.01)
*G01N 27/82* (2006.01)

(52) U.S. Cl.
CPC .............. *G01N 27/902* (2013.01); *G01N 27/82* (2013.01)
USPC ........................... 324/239; 324/225; 324/230

(58) Field of Classification Search
USPC .................................. 324/230, 239–243, 225
See application file for complete search history.

(56) References Cited

U.S. PATENT DOCUMENTS

| 3,449,661 A | * | 6/1969 | Puidak .......................... 324/237 |
| 4,303,885 A | * | 12/1981 | Davis et al. ................... 324/237 |
| 5,399,968 A | * | 3/1995 | Sheppard et al. ............. 324/242 |
| 6,014,024 A | * | 1/2000 | Hockey et al. ................ 324/240 |

FOREIGN PATENT DOCUMENTS

| JP | 06-27085 | 2/1994 |
| JP | 09-89844 | 4/1997 |
| JP | 2002-214202 | 7/2002 |
| JP | 2003-232776 | 8/2003 |
| JP | 2006-138784 | 6/2006 |
| JP | 2007-248169 | 9/2007 |
| JP | 2008-241285 | 10/2008 |

* cited by examiner

*Primary Examiner* — Jay Patidar
(74) *Attorney, Agent, or Firm* — Clark & Brody (57) ABSTRACT

In an eddy current testing method which involves using a rotatable eddy current testing probe in which a detection coil is arranged within an exciting coil, a change in detection sensitivity (a deviation of detection sensitivity) which changes depending on the rotational position of the detection coil is reduced. The eddy current testing probe includes an exciting coil EC1, a detection coil DC1, an exciting coil EC2 and a detection coil DC2, which are mounted on a disk DS. The eddy current testing probe is placed so as to face a circumferential surface of an object to be inspected T, which is in the shape of a circular cylinder, and the disk DS is rotated. Then, the distance (liftoff) between the detection coils DC1 and DC2 and an inspection surface changes. Therefore, also the detection sensitivity to a flaw signal changes. To reduce the change in detection sensitivity, the detection sensitivity is adjusted by detecting the rotational position (rotational angle) of the detection coils DC1 and DC2.

6 Claims, 8 Drawing Sheets

EDDY CURRENT TESTING METHOD AND APPARATUS FOR INSPECTING AN OBJECT FOR FLAWS

TECHNICAL FIELD

The present invention relates to an eddy current testing method and an eddy current testing apparatus.

BACKGROUND ART

There have conventionally been proposed eddy current testing probes in which a detection coil is arranged within an exciting coil so that coil planes of the both coils are orthogonal to each other and testing is performed while the detection coil is being rotated (refer to JP-A-2002-214202, for example).

A conventional eddy current testing probe will be described with reference to FIGS. 6A to 6C.

Figure 6A:
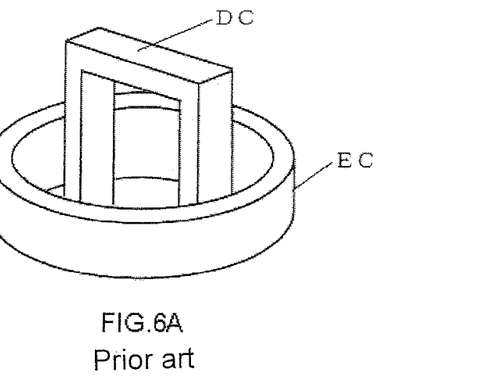
FIGS. 6A to 6C show the construction of a conventional eddy current testing probe which performs testing by rotating a detection coil.

As shown in FIG. 6A, the eddy current testing probe is provided with a pancake-shaped exciting coil EC and a quadrangular (empty square-shaped) detection coil DC, and the both coils are arranged so that coil planes are orthogonal to each other. The detection coil DC is rotated by a motor (not shown) around a central axis P of the exciting coil EC of FIG. 6B in the direction of the arrow. The exciting coil EC is arranged so that a coil plane thereof faces an inspection surface of an object to be inspected T.

Figure 6B:
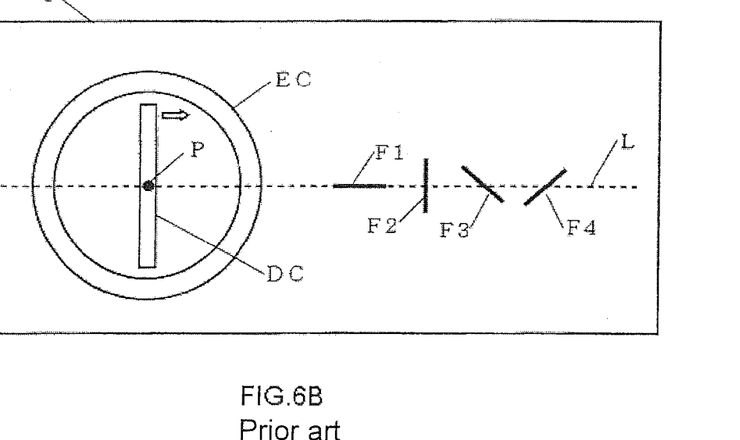
Figure 6C:
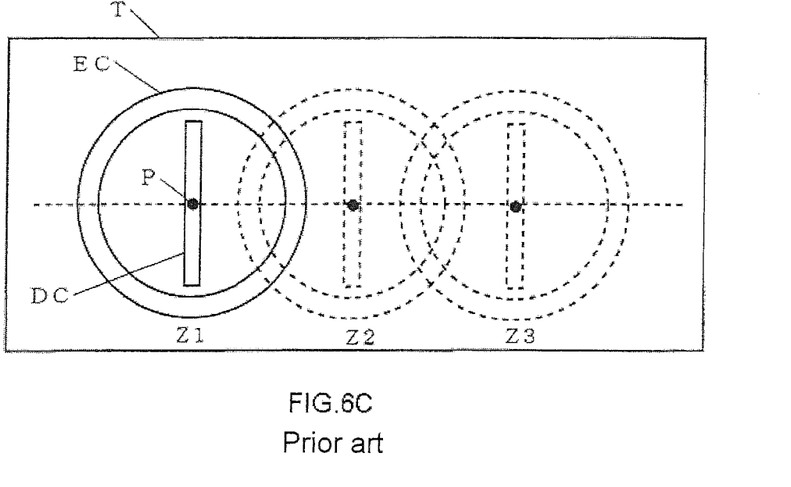

To detect flaws F1 to F4 in FIG. 6B in an object to be inspected T, the eddy current testing probe can be placed near the flaws and the detection coil DC can be rotated to detect the flaws F1 to F4 in any orientation. However, the range of the eddy current testing probe in which flaws can be detected is limited to within the range of the rotating detection coil DC. For this reason, when testing is performed along the line L as in FIG. 6C, for example, it is necessary that the eddy current testing probe be intermittently moved to the positions Z1, Z2 and Z3, and that the detection coil DC be rotated each time to perform testing. Therefore, the testing takes a long time.

Hence, there have been proposed eddy current testing probes which move at a prescribed speed while rotating a detection coil in order to permit continuous testing in a wide range (refer to JP-A-2007-248169, for example).

With reference to FIGS. 7A, 7B, and 7C1, 7C2, 7C3 and 7C4, a description will be given of a conventional eddy current testing probe which is moved while rotating a detection coil.

Figures 7A, 7B, 7C, 7C:
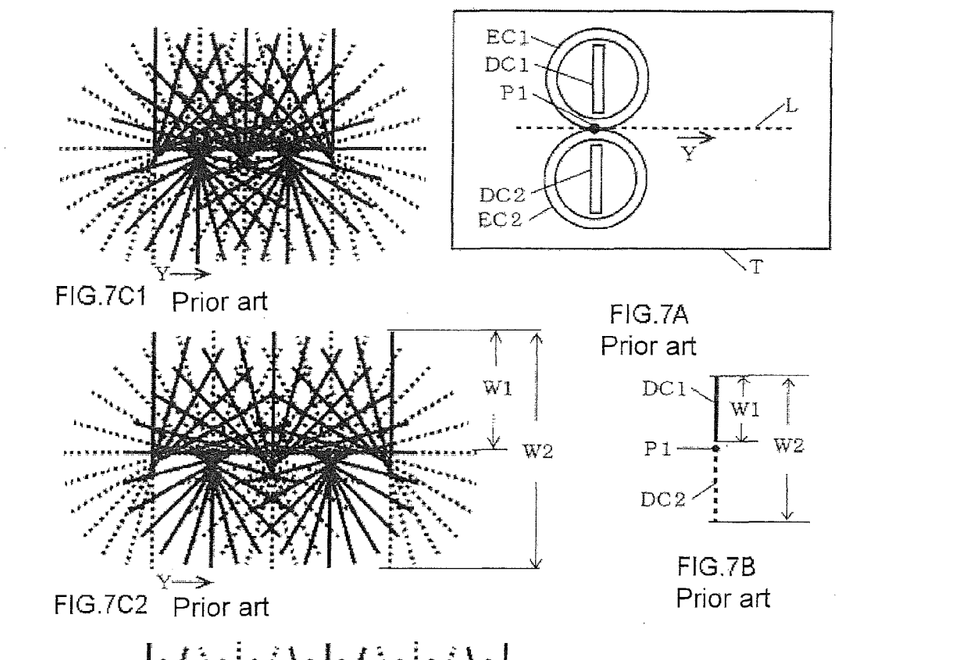

As shown in FIG. 7A, the eddy current testing probe is composed of a probe provided with an exciting coil EC1 and a detection coil DC1 and another probe provided with an exciting coil EC2 and a detection coil DC2; the two probes are mounted side by side on a disk (not shown). The disk moves in the Y-direction while rotating around a central axis P1.

The loci of the detection coils DC1 and DC2 obtained when the eddy current testing probe moves in the Y-direction are as shown in FIGS. 7C1 to 7C4. Specifically, for the distance S over which the eddy current testing probe moves in the Y-direction during one rotation of the detection coils DC1 and DC2, FIG. 7C1 shows loci obtained when S=0.75×W2, FIG. 7C2 shows loci obtained when S=1.0×W2, FIG. 7C3 shows loci obtained when S=1.5×W2, and FIG. 7C4 shows loci obtained when S=2.0×W2. In FIGS. 7C1 to 7C4, the solid lines indicate the loci of the detection coil DC1 and the broken lines indicate the loci of the detection coil DC2. As shown in FIG. 7B, W1 corresponds to the width of the detection coils DC1 and DC2, and W2 corresponds to a width which is twice as large as this width.

Figure 7C:
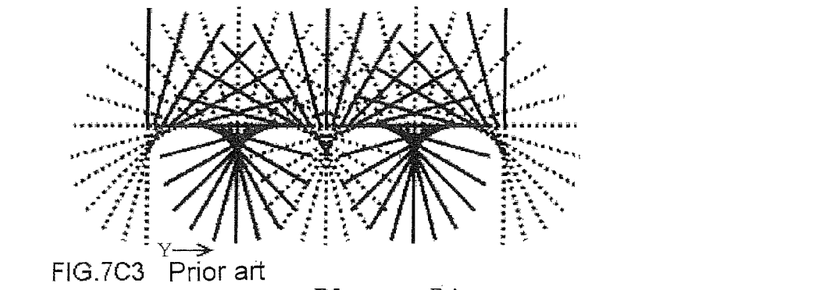

In the case of FIGS. 7C1 to 7C3, that is, in the case of the moving distance S=0.75×W2 to 1.5×W2, there is no region where the detection coils do not pass and, therefore, all flaws can be detected without omission in the range of W2, which corresponds to twice the width W1 of each detection coil.

Figure 7C:
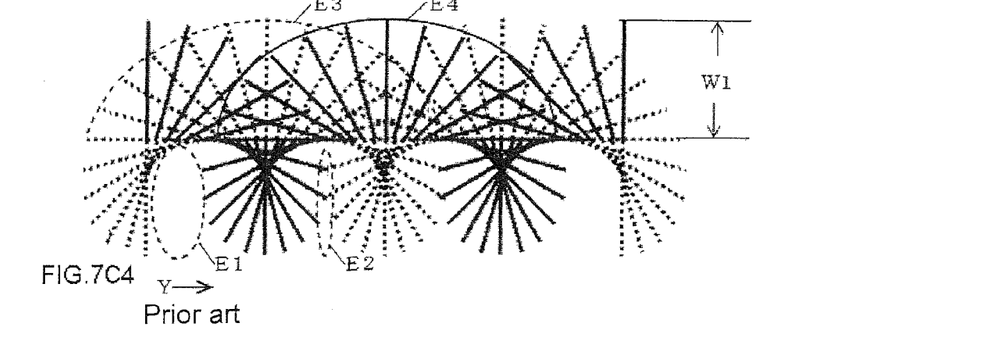

In the case of FIG. 7C4, that is, in the case of the moving distance S=2.0×W2, in the region E2, the loci of the detection coils are sparser and the testing accuracy decreases compared to regions of dense loci. Therefore, it is desirable to use the upper half region not containing the region E2 to perform testing. Note that no loci of the detection coils are indicated in the region E1 because the region corresponds to the start period of the detection coil rotation and hence the detection coils do not pass. When the detection coils have rotated half a rotation after the start of rotation, the loci are as shown in the region E2. In FIG. 7C4, the region E3 is a region where the detection coil DC2 passes and the region E4 is a region where the detection coil DC1 passes. The positions of the region E3 and the region E4 shift from each other by half a rotation (180 degrees) in the Y-direction.

SUMMARY OF THE INVENTION

In the eddy current testing probes shown in FIGS. 6A to 6C and FIGS. 7A to 7C4, the detection coil rotates and, therefore, when the inspection surface of an object to be inspected is not a flat surface (for example, an object to be inspected is in the shape of a circular cylinder, a cylindrical column and the like), the distance (liftoff) between the bottom of the detection coil and the inspection surface changes depending on the position of the detection coil. As a result, the detection sensitivity to flaw signals varies depending on the position of the detection coil.

Differences in detection sensitivity will be described with reference to FIGS. 8A to 8C.

Figure 8A:
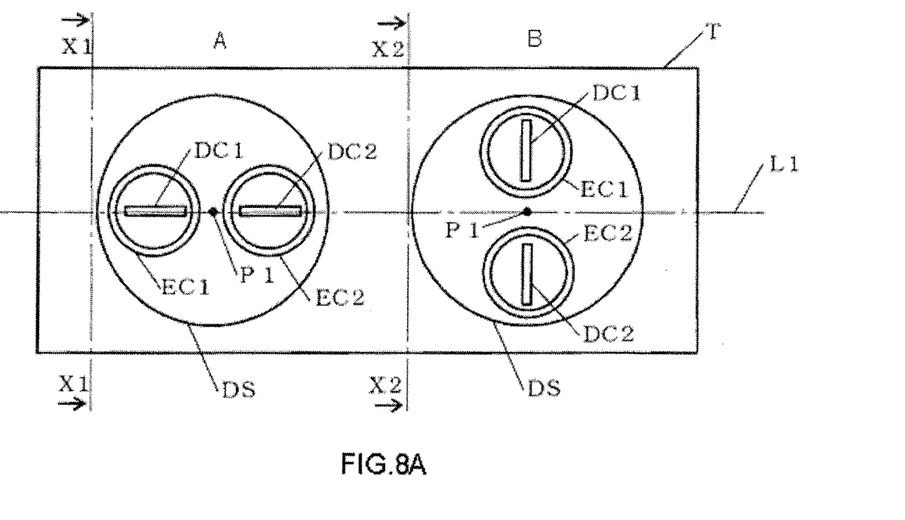
FIGS. 8A to 8C are diagrams to explain liftoffs when testing of an object to be inspected, which is in the shape of a circular cylinder, is performed by using the eddy current testing probe of FIGS. 7A to 7C4.
Figure 8B:
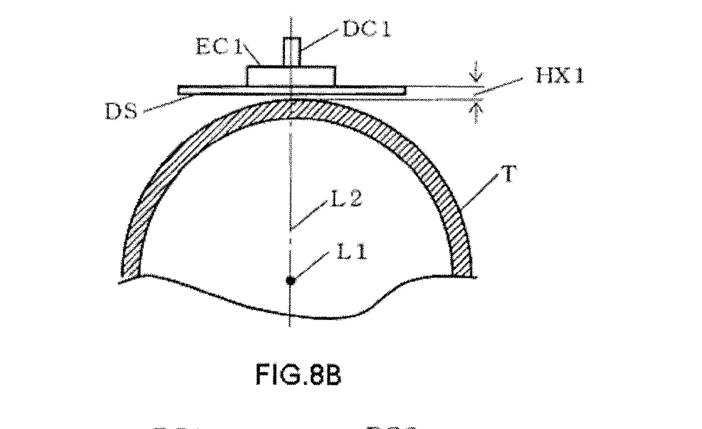
Figure 8C:
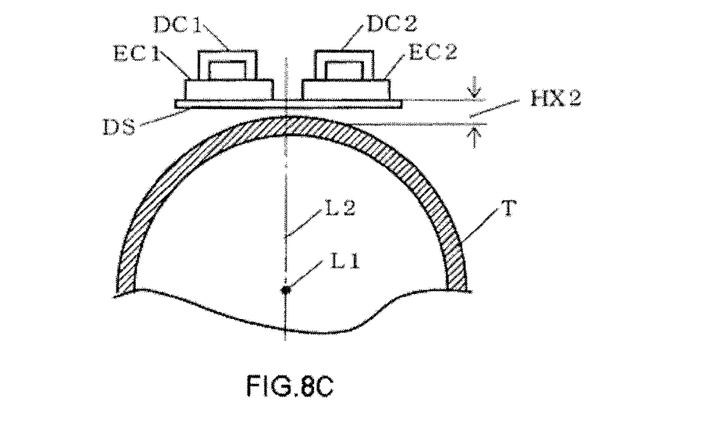

FIG. 8A is a plan view of eddy current testing probes placed so as to face a circumferential surface of an object to be inspected T, which is in the shape of a circular cylinder, FIG. 8B is a sectional view taken along the X1-X1 line of FIG. 8A, and FIG. 8C is a sectional view taken along the X2-X2 line of FIG. 8A.

In FIG. 8A, the detection coils DC1 and DC2 in a state A are stationary with the coil axes thereof being orthogonal to a central axis L1 of the object to be inspected T, and the detection coils DC1 and DC2 in a state B are stationary with the coil axes thereof being in parallel to the central axis L1.

If the distance (liftoff) between the bottom surfaces of the detection coils DC1 and DC2 of FIG. 8B and the inspection surface of the object to be detected T is HX1 and the distance (liftoff) between the central parts of bottom surfaces of the detection coils DC1 and DC2 of FIG. 8C and the inspection surface of the object to be detected T is HX2, then HX1 is smaller than HX2 (HX1<HX2). That is, the liftoff is smallest when the detection coils DC1 and DC2 are in the state A of FIG. 8A, and the liftoff is largest when the detection coils DC1 and DC2 are in the state B of FIG. 8A. Because the detection sensitivity to flaw signals of the detection coils DC1 and DC2 increases when the liftoff is small, the amplitude of signals of detected flaws increases. On the other hand, because the detection sensitivity to flaw signals of the detection coils DC1 and DC2 decreases when the liftoff is large, the amplitude of signals of detected flaws decreases.

Therefore, when the inspection surface is not a flat surface as in the case where the object to be inspected is in the shape of a circular cylinder and the like, the amplitude of flaw signals varies depending on the rotational position of the detection coil. In this case, therefore, flaw signals having a small amplitude may be misidentified and signal processing may be impeded if the amplitude of flaw signals varies.

In view of the above-described problems in eddy current testing probes which perform testing while rotating a detection coil, it is an object of the present invention to provide an eddy current testing method and an eddy current testing apparatus which provide small deviations of detection sensitivity to flaw signals due to the liftoff of the detection coil.

In order to achieve the object, a first aspect of the present invention provides an eddy current testing method which involves rotating an eddy current testing probe in which a detection coil is arranged within an exciting coil so that coil planes of the both coils are orthogonal to each other, and testing an object to be inspected in which the liftoff between an inspection surface of the object and the detection coil changes depending on the rotational position of the detection coil, characterized in that the detection sensitivity to a flaw signal is adjusted to a reference value of detection sensitivity, according to the rotational position of the detection coil.

A second aspect of the present invention provides an eddy current testing method which involves rotating an eddy current testing probe in which a detection coil is arranged within an exciting coil so that coil planes of the both coils are orthogonal to each other, and testing an object to be inspected in which the liftoff between an inspection surface of the object and the detection coil changes depending on the rotational position of the detection coil, characterized in that the detection sensitivity to a flaw signal is adjusted to a reference value of detection sensitivity, according to the liftoff depending on the rotational position of the detection coil.

A third aspect of the present invention provides the eddy current testing method according to claim 1 or 2, characterized in that the object to be inspected is a circular cylinder or a cylindrical column.

A fourth aspect of the present invention provides an eddy current testing apparatus which comprises a rotatable eddy current testing probe in which a detection coil is arranged within an exciting coil so that coil planes of the both coils are orthogonal to each other, and tests an object to be inspected in which the liftoff between an inspection surface of the object and the detection coil changes depending on the rotational position of the detection coil, characterized in that the eddy current testing apparatus comprises a detection device of rotational position which detects the rotational position of the detection coil and an adjustment device of detection sensitivity which adjusts the detection sensitivity to a flaw signal to a reference value of detection sensitivity, according to the rotational position detected by the detection device of rotational position.

A fifth aspect of the present invention provides an eddy current testing apparatus which comprises a rotatable eddy current testing probe in which a detection coil is arranged within an exciting coil so that coil planes of the both coils are orthogonal to each other, and tests an object to be inspected in which the liftoff between an inspection surface of the object and the detection coil changes depending on the rotational position of the detection coil, characterized in that the eddy current testing apparatus comprises a liftoff detection device which detects the liftoff depending on the rotational position of the detection coil and an adjustment device of detection sensitivity which adjusts the detection sensitivity to a flaw signal to a reference value of detection sensitivity, according to the liftoff detected by the liftoff detection device.

A sixth aspect of the present invention provides the eddy current testing apparatus according to claim 4 or 5, characterized in that the object to be inspected is a circular cylinder or a cylindrical column.

According to the present invention, testing is performed by rotating an eddy current testing probe in which a detection coil is arranged within an exciting coil so that coil planes of the both coils are orthogonal to each other. Therefore, it is possible to detect flaws in any orientation by using one eddy current testing probe and it is possible to continuously detect flaws in a wide range by moving the eddy current testing probe.

According to the present invention, the detection sensitivity to a flaw signal can be adjusted to a reference value of detection sensitivity by detecting a rotational position of the detection coil or the liftoff of the detection coil at the rotational position; hence it is possible to perform testing of an object to be inspected for which the liftoff between the detection coil and the inspection surface of the object changes depending on the rotational position of the detection coil with substantially constant detection sensitivity. Therefore, in testing, a flaw signal is not misidentified and the flaw signal can easily be processed.

According to the present invention, the liftoff can be indirectly detected (estimated) by detecting a rotational position of the detection coil; hence the liftoff can easily be detected and a construction of liftoff detection apparatus may be simple.

According to the present invention, a liftoff depending on a rotational position of the detection coil is directly measured and the detection sensitivity is adjusted according to the liftoff; hence the detection sensitivity can be accurately adjusted.

According to the present invention, it is possible to perform testing with substantially constant detection sensitivity if an object to be inspected is a circular cylinder.

BRIEF DESCRIPTION OF THE DRAWINGS

FIGS. 3A1 and 3A2 show the construction of an apparatus which detects the rotational position of the detection coil of the eddy current testing probe of FIGS. 1A to 1C and FIGS. 3B1 and 3B2 show the construction of an apparatus which detects liftoffs of the detection coil;

FIGS. 7A to 7C4 show the construction of a conventional eddy current testing probe which moves a detection coil while rotating the detection coil.

DESCRIPTION OF EMBODIMENT

An eddy current testing apparatus according to an embodiment of the present invention will be described with reference to FIGS. 1A to 1C to FIGS. 5A and 5B. Note that common parts in each drawing bear like reference numerals.

Figure 1A:
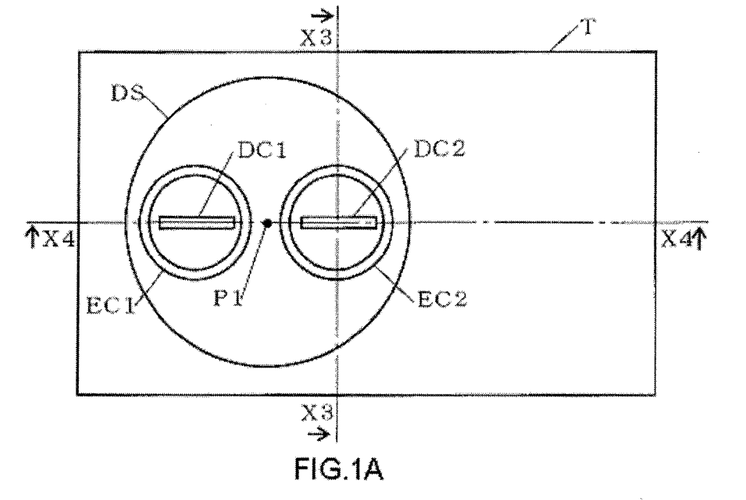
FIGS. 1A to 1C show the construction of an eddy current testing probe used in an eddy current testing apparatus according to an embodiment of the present invention.
Figure 1B:
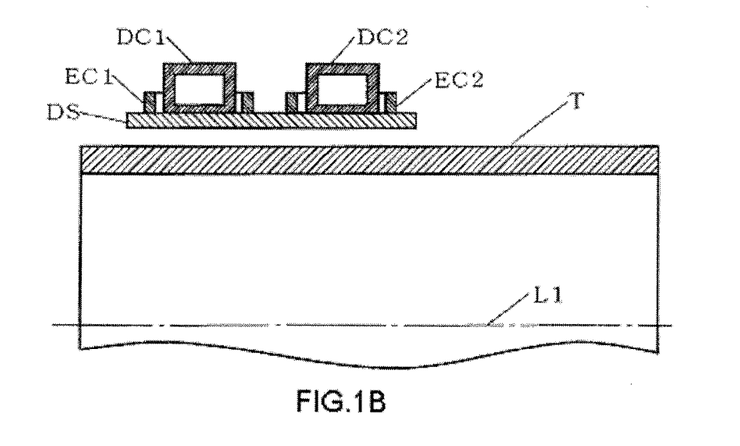
Figure 1C:
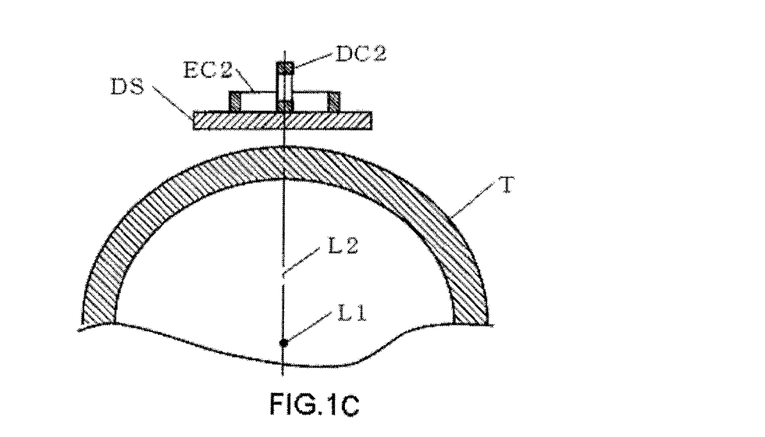

FIGS. 1A to 1C show the construction of an eddy current testing probe used in an eddy current testing apparatus according to an embodiment of the present invention.

FIG. 1A is a plan view of the eddy current testing probe, FIG. 1B is a sectional view taken along the X4-X4 line of FIG. 1A, and FIG. 1C is a sectional view taken along the X3-X3 line of FIG. 1A. Note that the construction and arrangement of an exciting coil and a detection coil are the same as in the eddy current testing probe of FIGS. 6A to 6C, FIGS. 7A to 7C4 and FIGS. 8A to 8C.

The eddy current testing probe of FIGS. 1A to 1C comprises a probe provided with an exciting coil EC1 and a detection coil DC1 and a probe provided with an exciting coil EC2 and a detection coil DC2. The two probes are mounted on a disk DS. The exciting coils EC1 and EC2 have the shape of a pancake (circular), and the detection coils DC1 and DC2 have the shape of a quadrangle (empty square-shaped) having an opening. The exciting coil EC1 and the detection coil DC1 are arranged so that coil planes of the both coils are orthogonal to each other (also the coil axes are orthogonal to each other), and the detection coil DC1 is arranged within the exciting coil EC1. Similarly, the exciting coil EC2 and the detection coil DC2 are arranged so that coil planes of the both coils are orthogonal to each other (also the coil axes are orthogonal to each other), and the detection coil DC2 is arranged within the exciting coil EC2.

The exciting coils EC1 and EC2 are arranged so that coil planes of the two coils face the plane of the disk DS, and the detection coils DC1 and DC2 are arranged so that the coil axes are parallel and the coil planes are arranged side by side on the same plane in the direction of the central axis L1 of an object to be inspected T. As shown in FIG. 1C, the disk DS is arranged so as to be orthogonal to the direction of the diameter L2 of the object to be inspected T, which is in the shape of a circular cylinder. The disk DS rotates by use of a motor (not shown) around a central axis P1 thereof.

Note that the shape of the exciting coils EC1 and EC2 is not limited to the shape of a pancake, but may also be the shape of an ellipse and the shape of a rectangle. The shape of the detection coils DC1 and DC2 is not limited to the shape of a quadrangle, but may also be the shape of a triangle, the shape of an ellipse and the shape of a circle. The exciting coils EC1 and EC2 may also be formed from one elliptic or rectangular exciting coil and the detection coils DC1 and DC2 may also be arranged within this one exciting coil. In this case, the eddy current testing probe becomes simple in construction. The detection coils DC1 and DC2 may also be arranged so that the coil axes of the two coils intersect with each other.

Next, with reference to FIGS. 2A to 2C, a description will be given of the relationship among the rotational position, liftoff and detection sensitivity of a detection coil of the eddy current testing probe of FIGS. 1A to 1C.

Figure 2A:
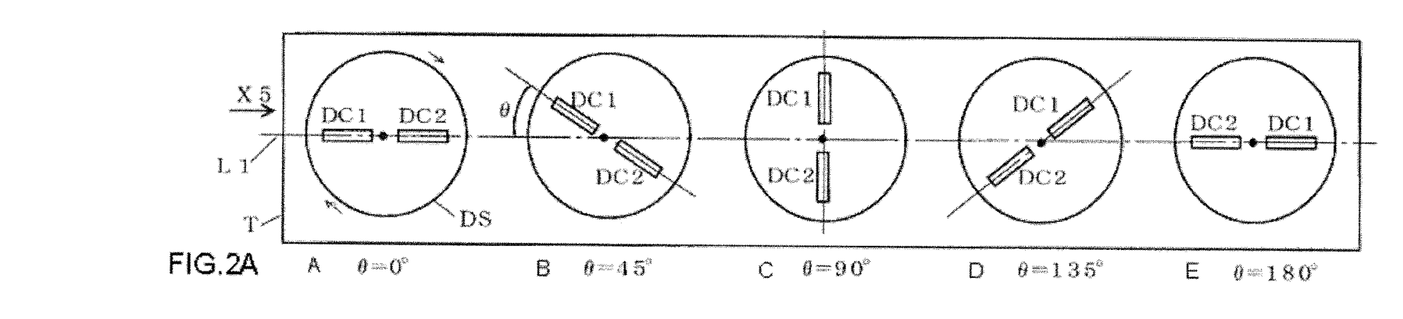
FIGS. 2A to 2C show the relationship among the rotational positions of a detection coil of the eddy current testing probe of FIGS. 1A to 1C, liftoff and detection sensitivity.
Figures 2B, 2C:
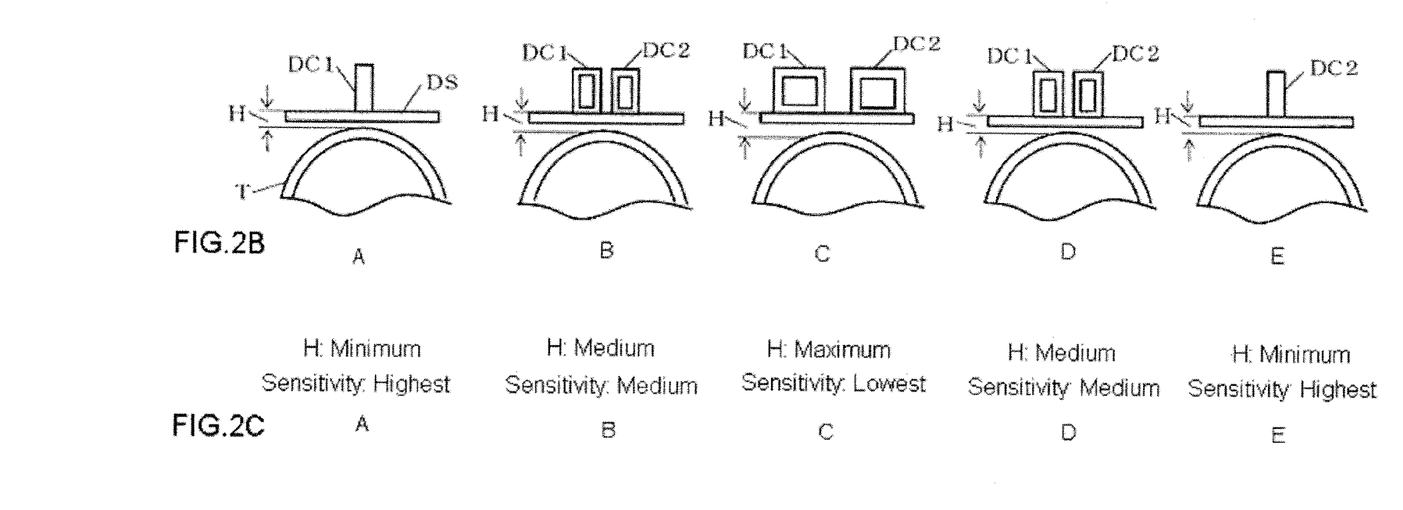

A to E of FIG. 2A indicate the rotational positions (rotational angles) of the detection coils DC1 and DC2, and the rotational positions are those obtained when the angle θ of the coil planes of the detection coils DC1 and DC2 formed with the direction of the central axis L1 of an object to be inspected T is θ=0 degrees, 45 degrees, 90 degrees, 135 degrees and 180 degrees, respectively. FIG. 2B shows side views and liftoff H at the rotational positions A to E in the X5 direction of FIG. 2A, and FIG. 2C shows the liftoff and magnitude of the detection sensitivity to flaw signals at these rotational positions.

The liftoff H and detection sensitivity at the rotational positions A to E are discussed: the distance (liftoff) between the central parts of bottom surfaces (end surfaces on the inspection surface side) of the detection coils DC1 and DC2 and the inspection surface is smallest in the rotational positions A and E and largest in the rotational position C; and the detection sensitivity is highest in the rotational positions A and E and lowest in the rotational position C. The liftoff and detection sensitivity at the rotational positions B and D have intermediate values of the liftoff and detection sensitivity between the values in the rotational positions A and C. That is, the liftoff is smallest and the detection sensitivity is highest when the coil planes of the detection coils DC1 and DC2 are parallel to the direction of the central axis L1 of the object to be inspected T, and the liftoff is largest and the detection sensitivity is lowest when the coil planes of the detection coils DC1 and DC2 are orthogonal to the direction of the central axis L1 of the object to be inspected T.

The detection sensitivity changes depending on the liftoff, and the liftoff changes depending on the rotational position (rotational angle) of the detection coils DC1 and DC2. That is, because a change in the detection sensitivity depends on a change in the liftoff and a change in the liftoff depends on a change in the rotational position, the detection of the rotational position corresponds to the detection of the liftoff. Therefore, by detecting the rotational position of the detection coils DC1 and DC2, it is possible to indirectly detect (estimate) the liftoff at the rotational position, and a change in the detection sensitivity can be adjusted according to the detected rotational position. The liftoff at each rotational position is directly measured and a change in the detection sensitivity can be more precisely adjusted according to the measured liftoff.

Because the liftoff is a distance between the detection coils DC1 and DC2 and the inspection surface of an object to be inspected T, the liftoff changes depending on the curvature of the object to be inspected T.

Note that the angle θ is any of the rotational angle of the detection coils DC1 and DC2, the rotational angle of one set of probes composed of a probe provided with the detection coil DC1 and the exciting coil EC1 and another probe provided with the detection coil DC2 and the exciting coil EC2, and the rotational angle of the disk DS on which these probes are mounted.

It has been found, from the experiment results of the detection sensitivity to flaw signals described below, that the detection sensitivity at the rotational positions A and E of FIG. 2A is twice to three times the detection sensitivity at the rotational position C.

Various conditions of the experiment are as follows:

A pancake-shaped coil having a wire diameter of 0.16 mm, 180 coil turns and an inside diameter of 2.5 mm was used as the exciting coil of the eddy current testing probe, and a quadrangular (empty square-shaped) coil having a wire diameter of 0.05 mm, 120 coil turns and a width (width in the diametrical direction of the exciting coil) of 1.5 mm was used as the detection coil. The experiment was conducted by setting the spacing of the two detection coils (distance of the central parts of bottoms) at 8.4 mm and 14 mm. A steel pipe having a diameter of 73 mm in which a flaw 25 mm long, 0.3 mm wide and 0.5 mm deep was formed in the direction of the rotational positions A to D of FIG. 2A was used as the object to be inspected T. The testing of the surface of the object to be inspected T was performed in the circumferential direction by rotating the disk DS at 5000 rpm and rotating the object to be inspected T around the central axis L1 at 30 rpm.

As a result of the experiment results described above, the following adjustments may reduce a deviation of detection sensitivity to an extent which does not pose a problem in practical use: when the detection sensitivity at the rotational positions A and E (obtained when the coil planes of the detection coils DC1 and DC2 are parallel to the direction of the central axis L1 of the object to be inspected T) is set as a reference value, the detection sensitivity at the rotational position C (obtained when the coil planes of the detection coils DC1 and DC2 are orthogonal to the direction of the central axis L1 of the object to be inspected T) may be adjusted to twice to three times the reference value; alternatively, when the detection sensitivity at the rotational position C is set as a reference value, the detection sensitivity at the rotational positions A and E may be adjusted to ½ to ⅓ of the reference value; and the detection sensitivity at a position between the rotational positions A and E and the rotational position C may be adjusted at a linear ratio between the reference value and twice to three times the reference value or between the reference value and ½ to ⅓ of the reference value. That is, for a rotational position in which the detection sensitivity is highest and a rotational position in which the detection sensitivity is lowest, the detection sensitivity is adjusted on the basis of the detection sensitivity at one rotational position as a reference value so that the detection sensitivity at the two rotational positions becomes almost equal and the detection sensitivity at a position between the two rotational positions is adjusted at a linear ratio on the basis of the detection sensitivity at the two rotational positions.

Note that a deviation of the detection sensitivity which depends on the rotational position of the detection coil changes depending on the curvature of an object to be inspected; if a more precise adjustment of the detection sensitivity is desired, therefore, it is alternatively possible to store, in a memory and the like, curvature-detection sensitivity deviation characteristics which represent the relationship between the curvature of an object to be inspected and a deviation of the detection sensitivity which depends on the rotational position of the detection coil, and then prior to the start of testing, curvature-detection sensitivity deviation characteristics corresponding to the curvature of the object to be inspected may be selected to set in an adjustment device of detection sensitivity.

Although in the above-described embodiment, the description was given of the case where a reference value of detection sensitivity is maximum detection sensitivity or minimum detection sensitivity, other reference values of detection sensitivity, for example, detection sensitivity at the rotational position B (θ=45 degrees) may also be adopted as a reference value. In this case, adjustments are made so that the detection sensitivity at the rotational position A (θ=0 degrees) becomes low and adjustments are made so that the detection sensitivity at the rotational position C (θ=90 degrees) becomes high.

Figure 3A:
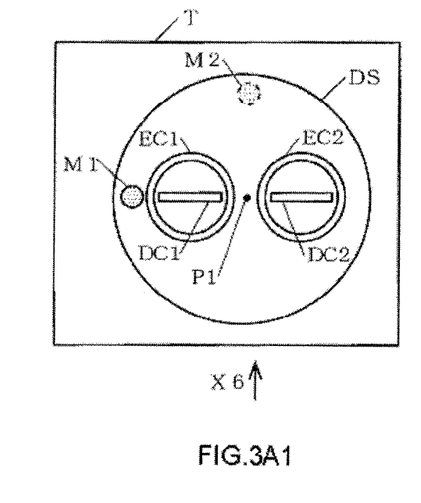

FIGS. 3A1 and 3A2 show the construction of an apparatus which detects the rotational position of the detection coil, and FIGS. 3B1 and 3B2 show the construction of an apparatus which detects liftoffs.

FIGS. 3A1 and 3B1 are plan views, and FIGS. 3A2 and 3B2 are X6 direction side views of FIGS. 3A1 and 3B1, respectively.

Figure 3A:
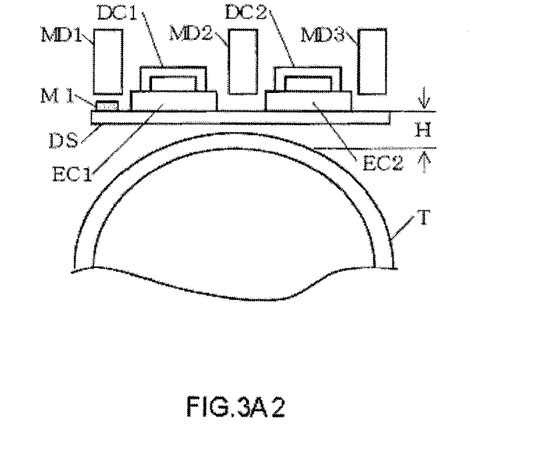

First, FIGS. 3A1 and 3A2 will be described.

FIGS. 3A1 and 3A2 show an example of an apparatus which detects the rotational position (rotational angle) of the detection coil. Note that, in FIG. 3A1, photodetectors MD1 to MD4 are omitted.

The disk DS is provided with a reflecting mirror M1 in an extension of the coil planes of the detection coils DC1 and DC2 arranged side by side, and the disk DS rotates around a central axis P1. When the disk DS rotates, also the reflecting mirror M1 rotates with the disk DS. On mounting members (not shown) other than the disk DS, four photodetectors MD1 to MD4 (MD4 is not shown) are arranged at intervals of 90° along the locus of the reflecting mirror M1. The positions of the photodetectors MD1 to MD4 correspond to the positions of θ=0 degrees, 90 degrees, 180 degrees and 270 degrees in FIG. 2A, respectively. The photodetectors MD1 to MD4 generate a position signal each time the reflecting mirror M1 passes. Due to position signals of the photodetectors MD1 to MD4, for example, it is possible to detect the rotational position or rotational angle of the detection coils DC1 and DC2 from a reference position of an object to be inspected T in the central axis direction (θ=0 degrees of FIG. 2A).

Specifically, a light source and a photo-detecting element are incorporated in each of the photodetectors MD1 to MD4. When the reflecting mirror M1 is present below the photodetectors MD1 to MD4, the light emitted from the light sources of the photodetectors MD1 to MD4 is reflected by the reflecting mirror M1 and is detected by the photo-detecting elements of the photodetectors MD1 to MD4. On the other hand, when the reflecting mirror M1 is not present below the photodetectors MD1 to MD4, the light emitted from the light sources of the photodetectors MD 1 to MD4 is radiated onto an upper surface of the disk DS. If at least the upper surface of the disk DS is formed from a material of low reflectance, the reflected light of the light radiated onto the upper surface of the disk DS becomes scarcely detected by the photo-detecting elements of the photodetectors MD1 to MD4. If the photodetectors MD1 to MD4 are configured to generate prescribed electrical signals (position signals) when the amount of light received by the photo-detecting elements of the photodetectors MD1 to MD4 has become large, then it is possible to distinguish whether or not the reflecting mirror M1 is present below the photodetectors MD1 to MD4.

The mounting position of the reflecting mirror M1 is not limited to the position shown in the figures, but the reflecting mirror M1 may also be mounted in the position M2, which is 90 degrees apart from the reflecting mirror M1. In this case, when the disk DS rotates clockwise, by delaying position signals of the photodetectors MD1 to MD4 90 degrees, these signals become the same as position signals for the reflecting mirror M1.

In the case of the apparatus of FIGS. 3A1 and 3A2, a light source of a light-emitting diode and the like may also be used in place of the reflecting mirror M1. Of the light source and the photo-detecting element described above, when a light source such as a light-emitting diode is used in place of the reflecting mirror M1, only the photo-detecting elements may be incorporated in the photodetectors MD1 to MD4, without the need of incorporating the light source.

In the apparatus of FIGS. 3A1 and 3A2, although four photodetectors MD1 to MD4 are shown, the number of photodetectors is not limited to four, and more photodetectors may be used by arranging them at intervals of 45 degrees, for example. In this case, it is possible to more precisely detect the rotational position of the detection coils DC1 and DC2. When still further precise detection of the rotational position of the detection coils DC1 and DC2 is desired, a rotational angle sensor (a rotary encoder) may also be attached to a rotary shaft of the disk DS.

Because the apparatus of FIGS. 3A1 and 3A2 can detect the rotational position (rotational angle) of the detection coil only by detecting position signals produced when the reflecting mirror, light source and the like mounted on the disk DS pass by the photodetector, the construction of the apparatus becomes simple.

Next, FIGS. 3B1 and 3B2 will be described. Note that, in FIGS. 3B1 and 3B2, the symbols for the exciting coil and the detection coil are omitted (the same as in FIGS. 3A1 and 3A2). In FIG. 3B1, laser distance meters LD11 to LD22 are omitted.

Figure 3B:
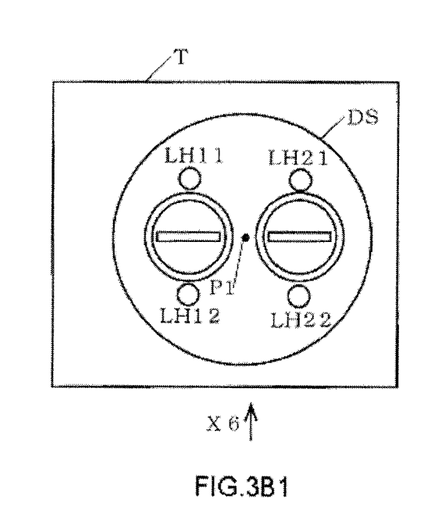
Figure 3B:
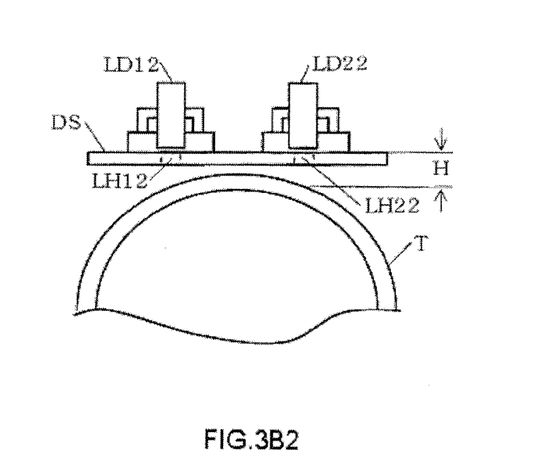

FIGS. 3B1 and 3B2 show an example of an apparatus which directly measures the distance (liftoff) H between the central parts of bottom surfaces of the detection coils DC1 and DC2 and the inspection surface of an object to be inspected T.

In the disk DS, light-transmitting portions (transmission holes) LH11 and LH12 are formed on both external sides of the exciting coil EC1 along the coil axis direction of the detection coil DC1, and light-transmitting portions LH21 and LH22 are formed on both external sides of the exciting coil EC2 along the coil axis direction of the detection coil DC2. The disk DS rotates around a central axis P1. The laser distance meters LD11 and LD12 (only the LD12 is shown) face the light-transmitting portions LH11 and LH12, respectively, and the laser distance meters LD21 and LD22 (only the LD22 is shown) face the light-transmitting portions LH21 and LH22, respectively. The four laser distance meters LD11 to LD22 rotate with the disk DS, while kept opposed to the light-transmitting portions LH11 to LH22.

The laser distance meters LD11 to LD22 project light onto the inspection surface of the object to be inspected T via the light-transmitting portions LH11 to LH22, receive the reflected light from the inspection surface, and measure the liftoff depending on the rotational position (rotational angle) of the detection coils DC1 and DC2. The liftoff of the detection coil DC1 is found by averaging liftoffs measured by the laser distance meters LD11 and LD12, and the liftoff of the detection coil DC2 is found by averaging liftoffs measured by the laser distance meters LD21 and LD22.

Because the apparatus of FIGS. 3B1 and 3B2 directly measures liftoffs at each rotational position of the detection coils, it is possible to precisely adjust the detection sensitivity at each rotational position. Note that liftoffs can be measured by using an eddy-current type displacement gauge in addition to the laser distance meter described in this embodiment. Liftoffs can also be measured on the basis of a change in the impedance of the exciting coils EC1 and EC2.

Figure 4A:
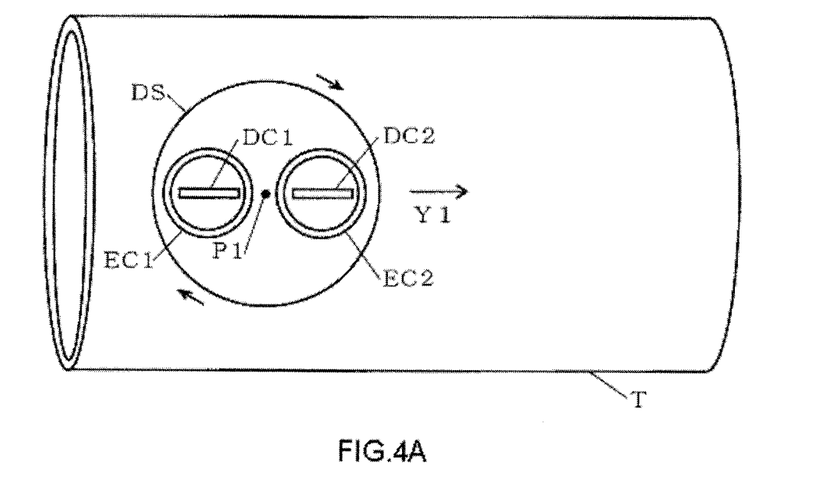
FIGS. 4A and 4B are diagrams to explain the movement of the eddy current testing probe and the rotation of an object to be inspected when testing of the object to be inspected, which is in the shape of a circular cylinder, is performed by using the eddy current testing probe of FIGS. 1A to 1C.
Figure 4B:
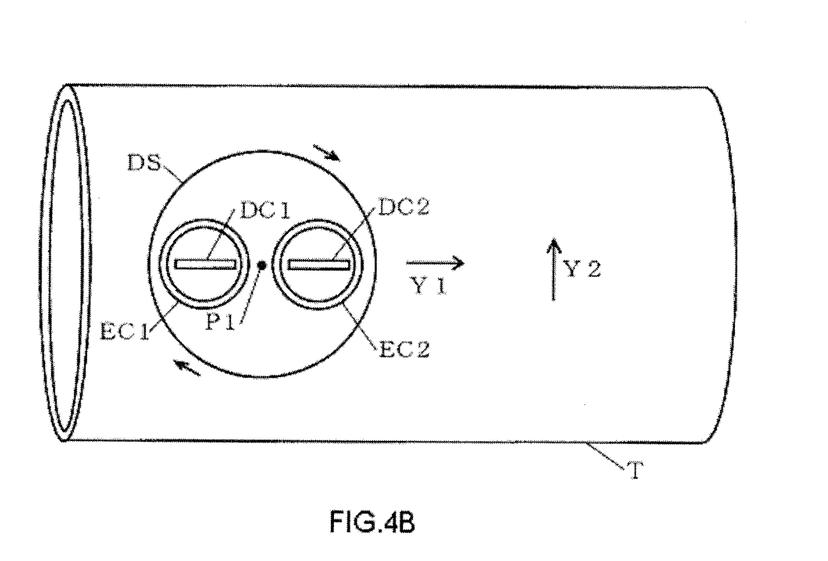

FIGS. 4A and 4B are diagrams to explain the movement of an eddy current testing probe of FIGS. 1A to 1C and the rotation of an object to be inspected, which is in the shape of a circular cylinder, when testing of the object to be inspected is performed by use of the eddy current testing probe.

FIG. 4A shows an example in which testing is performed by moving the eddy current testing probe in the Y1 direction while the disk DS is being rotated in the direction of the arrows (clockwise) around a central axis P1. FIG. 4B shows an example in which testing is performed by moving the eddy current testing probe in the Y1 direction and rotating the object to be inspected T around the central axis thereof in the Y2 direction while the disk DS is being rotated clockwise. In the case of FIG. 4B, the eddy current testing probe may be rotated in the circumferential direction of the object to be inspected T instead of rotating the object to be inspected T.

Figure 5A:
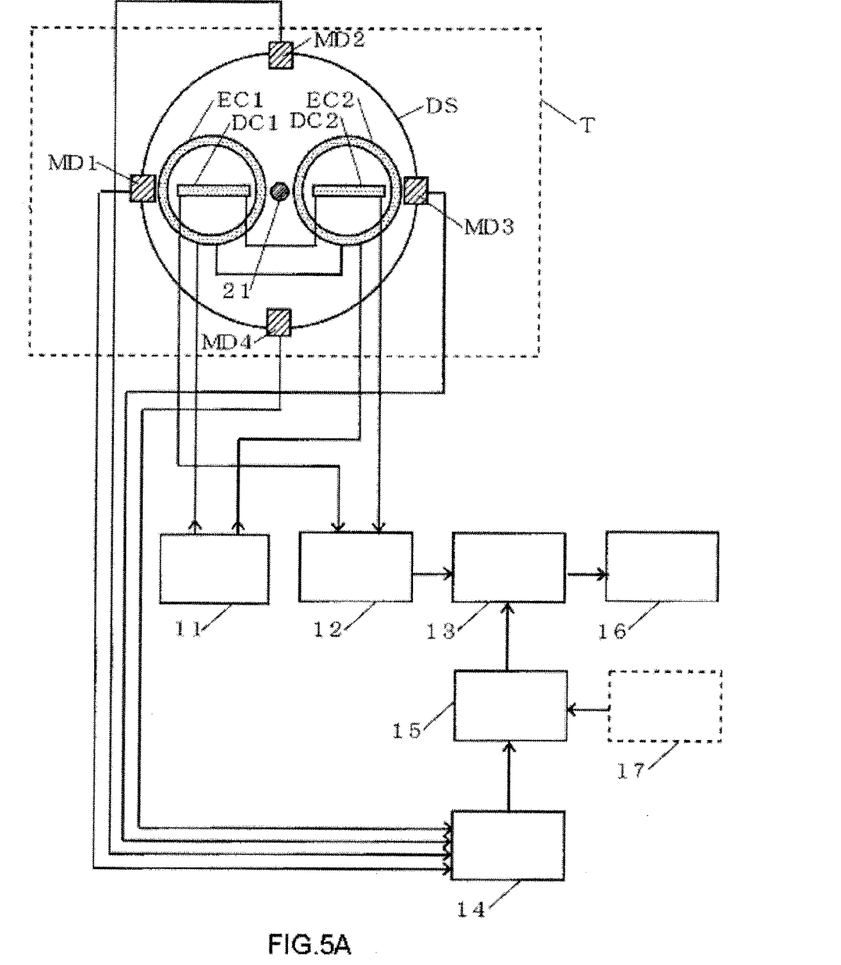
FIGS. 5A and 5B show the construction of an eddy current testing apparatus in which the eddy current testing probe of FIGS. 1A to 1C is used.
Figure 5B:
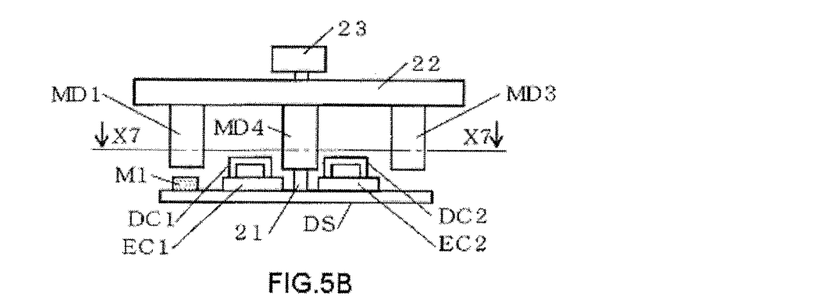

FIGS. 5A and 5B show the construction of an eddy current testing apparatus in which the eddy current testing probe of FIGS. 1A to 1C is used.

FIG. 5A shows a plan view of the eddy current testing probe placed so as to face an object to be inspected T (a plan view taken along the X7-X7 line of FIG. 5B (a partial sectional view)) and a block diagram of the eddy current testing apparatus, and FIG. 5B shows a side view of the eddy current testing probe.

The disk DS is provided with exciting coils EC1 and ED2, which are connected in series, detection coils DC1 and DC2, which are connected in series, and a reflecting mirror M1, and the disk DS is mounted on a rotary shaft 21. The rotary shaft 21 is rotated by a motor 23. Photodetectors MD1, MD2, MD3 and MD4 are mounted on a mounting member 22, and are arranged at intervals of 90 degrees. The arrangement intervals of the photodetectors are not limited to 90 degrees, and a more precise detection of the rotational position is possible if the arrangement intervals are set to 45 degrees or smaller angles.

The exciting coils EC1 and EC2 generate an eddy current on the inspection surface of the object to be inspected T by an exciting current supplied from a power supply device 11 of exciting current. If there is a flaw on the inspection surface of the object to be inspected T, fluctuations occur in the eddy current and a voltage is induced by the fluctuations of the eddy current in the detection coils DC1 and DC2. The induced voltage of the detection coils DC1 and DC2 is supplied to a generation device 12 of flaw signal. The generation device 12 of flaw signal generates a flaw signal on the basis of the induced voltage and supplies this flaw signal to an amplitude adjustment device (a gain adjustment device) 13.

Each time the reflecting mirror M1 of the disk DS passes, the photodetectors MD1, MD2, MD3 and MD4 generate position signals and supply the position signals to a detection device 14 of rotational position (a detection device of rotational angle). On the basis of the position signals the detection device 14 of rotational position detects the rotational position (rotational angle) of the detection coils DC1 and DC2. On the basis of a rotational position (for example, θ=0 degrees of FIG. 2A) corresponding to a reference value of detection sensitivity (for example, maximum detection sensitivity) and a rotational position detected by the detection device 14 of rotational position, an adjustment device 15 of detection sensitivity finds an adjustment amount of detection sensitivity, and generates an adjustment signal of detection sensitivity corresponding to this adjustment amount of detection sensitivity. The amplitude adjustment device 13 adjusts the amplitude of the flaw signal according to the adjustment signal detection sensitivity. The amplitude of the flaw signal of the amplitude adjustment device 13 becomes substantially constant regardless of the rotational position of the detection coils DC1 and DC2.

Specifically, the detection device 14 of rotational position counts, for example, an elapsing time since the time of supply of a position signal from the photodetector MD1. And by multiplying this counted elapsing time by a rotating speed set value of the disk DS which has been inputted beforehand, the detection device 14 of rotational position calculates an amount of change in the rotational position by using the rotational position where the reflecting mirror M1 is opposed to the photodetector MD1 (i.e., the rotational position at the time of supply of the position signal from the photodetector MD1) as a starting time of calculation. Next, at the same time with the supply of a position signal from the photodetector MD2, the detection device 14 of rotational position clears the above-described counted elapsing time to zero and newly counts an elapsing time since the time of supply of the position signal from the photodetector MD2. And by multiplying this counted elapsing time by the rotating speed set value of the disk DS, the detection device 14 of rotational position calculates an amount of change in the rotational position by using the rotational position where the reflecting mirror M1 is opposed to the photodetector MD2 (i.e., the rotational position at the time of supply of the position signal from the photodetector MD2) as a starting time of calculation. After that, by repeating the same procedure, the detection device 14 of rotational position detects the rotational position of the coils DC1 and DC2 (for example, a rotational position obtained when θ=0 degrees of FIG. 2A is a reference position).

The flaw signal of the amplitude adjustment device 13 is displayed in a display and storage device 16 of flaw signal. As required, the flaw signal is stored in a memory and the like.

Note that a deviation of the detection sensitivity which depends on relative to the rotational position of the detection coil changes depending on the curvature of an object to be inspected; therefore, it is alternatively possible to store, in a memory and the like of a storage device 17 of curvature-detection sensitivity, curvature-detection sensitivity deviation characteristics which represent the relationship between the curvature of an object to be inspected and a deviation of the detection sensitivity which depends on a rotational position of the detection coil, and then prior to the start of testing, curvature-detection sensitivity deviation characteristics corresponding to the curvature of the object to be inspected may be selected to set in the adjustment device 15 of detection sensitivity. In this case, it is also possible to ensure that the curvature-detection sensitivity deviation characteristics are automatically selected when the curvature of an object to be inspected is inputted to the storage device 17 of curvature-detection sensitivity.

In the eddy current testing apparatus of FIGS. 5A and 5B, it is also possible to use an apparatus which directly measures the liftoff at each rotational position of the detection coil (for example, the device of FIGS. 3B1 and 3B2) in place of the reflecting mirror and the photodetectors. In this case, measured liftoffs are taken into the detection device 14 of rotational position.

Although in this embodiment, the description was given of the case where the shape of an object to be inspected is the shape of a circular cylinder, the shape of the object to be inspected is not limited to a circular cylinder. The object to be inspected may also be objects in which the distance (liftoff) between the detection coil and the inspection surface of the object to be inspected changes depending on the rotational position of the detection coil, such as an elliptical cylinder, a cylindrical column and an elliptical column.

The invention claimed is:

1. An eddy current testing method which involves for rotating an eddy current testing probe in which a detection coil is arranged within an exciting coil so that coil planes of the both coils are orthogonal to each other, and testing an object to be inspected in which a liftoff between an inspection surface of the object and the detection coil changes depending on a rotational position of the detection coil, comprising the steps of:
  setting a detection sensitivity to a flaw signal at a predetermined rotational position of the detection coil as a reference value of detection sensitivity; and
  adjusting a detection sensitivity to a flaw signal at a rotational position of the detection coil based on the reference value of detection sensitivity,
  wherein the inspection surface of the object has a predetermined curvature so that the liftoff oscillates between a maximum value and a minimum value in a continuous fashion depending on the rotational position of the detention coil.

2. The eddy current testing method according to claim 1, wherein the object to be inspected is a circular cylinder or a cylindrical column.

3. An eddy current testing method for rotating an eddy current testing probe in which a detection coil is arranged within an exciting coil so that coil planes of the both coils are orthogonal to each other, and testing an object to be inspected in which a liftoff between an inspection surface of the object and the detection coil changes depending on a rotational position of the detection coil, comprising the steps of:
  setting a detection sensitivity to a flaw signal corresponding to the liftoff depending on a predetermined rotational position of the detection coil as a reference value of detection sensitivity; and
  adjusting a detection sensitivity to a flaw signal corresponding to the liftoff depending on a rotational position of the detection coil based on the reference value of detection sensitivity,
  wherein the inspection surface of the object has a predetermined curvature so that the liftoff oscillates between a maximum value and a minimum value in a continuous fashion depending on the rotational position of the detection coil.

4. An eddy current testing apparatus which comprises a rotatable eddy current testing probe in which a detection coil is arranged within an exciting coil so that coil planes of the both coils are orthogonal to each other, and tests an object to be inspected in which a liftoff between an inspection surface of the object and the detection coil changes depending on a rotational position of the detection coil, comprising:
  a detection device of rotational position which detects a rotational position of the detection coil; and
  an adjustment device of detection sensitivity which sets a detection sensitivity to a flaw signal at a predetermined rotational position of the detection coil as a reference value of detection sensitivity and adjusts a detection sensitivity to a flaw signal at a rotational position detected by the detection device of rotational position based on the reference value of detection sensitivity,
  wherein the inspection surface of the object has a predetermined curvature so that the liftoff oscillates between a maximum value and a minimum value in a continuous fashion depending on the rotational position of the coil.

5. The eddy current testing apparatus according to claim 4, wherein the object to be inspected is a circular cylinder or a cylindrical column.

6. An eddy current testing apparatus which comprises a rotatable eddy current testing probe in which a detection coil is arranged within an exciting coil so that coil planes of the both coils are orthogonal to each other, and tests an object to be inspected in which a liftoff between an inspection surface of the object and the detection coil changes depending on a rotational position of the detection coil, comprising:
  a liftoff detection device which detects the liftoff depending on the rotational position of the detection coil; and
  an adjustment device of detection sensitivity which sets a detection sensitivity to a flaw signal corresponding to the liftoff depending on a predetermined rotational position of the detection coil as a reference value of detection sensitivity and adjusts a detection sensitivity to a flaw signal corresponding to a liftoff detected by the liftoff detection devise based on the reference value of detection sensitivity,
  wherein the inspection surface of the object has a predetermined curvature so that the liftoff oscillates between a maximum value and a minimum value in a continuous fashion depending on the rotational position of the detection coil.

* * * * *